United States Patent [19]

Thornton

[11] 4,008,727
[45] Feb. 22, 1977

[54] INTERPROXIMAL SPACE TOOTH CLEANER

[76] Inventor: Thomas F. Thornton, 221 Mill Road, New Canaan, Conn. 06840

[22] Filed: May 19, 1975

[21] Appl. No.: 578,880

[52] U.S. Cl. .................................................. 132/89
[51] Int. Cl.² .......................................... A61C 15/00
[58] Field of Search ...................... 132/89, 92 A, 93

[56] References Cited

UNITED STATES PATENTS

| 1,069,874 | 8/1913 | Hanscom | 132/93 |
| 3,744,499 | 7/1973 | Wells | 132/92 A |
| 3,896,824 | 7/1975 | Thornton | 132/89 |

Primary Examiner—G.E. McNeill
Attorney, Agent, or Firm—Ernest M. Junkins

[57] ABSTRACT

A variable diameter tooth cleaner formed by a plurality of elongate filaments to have a brush portion and a string portion with the string portion having two parts and with the brush portion being placed between the two parts. The string parts may be flexible or for spaces associated with fixed bridges may be formed with a rigid end extent for enabling insertion by pushing into the spaces.

1 Claim, 3 Drawing Figures

INTERPROXIMAL SPACE TOOTH CLEANER

In my copending application, Ser. No. 361,237, filed May 17, 1973, now U.S. Pat. No. 3,896,824 granted July 29, 1975, and entitled Teeth Cleaning there is disclosed an elongate cleaner for passage through the interproximental spaces formed between adjacent teeth. The cleaner is formed from a length of textured yarn that is composed of a plurality of elongate, randomly crinkled, filaments with the filaments being coated with a hardened covering. A portion of the filaments is left crinkled to form a brush portion, while the covering maintains the remainder of the length of the filaments, straight and parellel, i.e., uncrinkled, to form a string portion. The string portion filaments are quite readily separable thereby rendering the string portion flexible. Heretofore such a cleaner has been constructed with a brush portion integral with the string portion but at one or both ends of the cleaner. The user passes the string portion through the contact points of the space and then pulls on the string to draw the brush portion through the space.

While such a construction has been found quite satisfactory, there has appeared a tendency of some of the brush filaments to snag or catch on rough edges or projections of the teeth defining the space. A user accustomed to only pulling the string portion, may continue to do so and cause breakage of some of the snagged filaments. Further pulling has caused the broken snagged filaments to be shredded from the cleaner and be left in the space where, as they were small in length, they could be somewhat difficult to remove. Also, if it is desired to pass the brush portion through the space a plurality of times in different directions, the string portion each time had to be forced through the contact points.

The cleaner had heretofore been usable only between teeth having somewhat separable contact points through which the string portions may pass. This excluded its use between teeth constituting part of a fixed bridge where the space was bridged by dental structure and the string portion, by reason of its flexibility, could not be forced into or through such a space. Additionally, a user had difficulty in rubbing the brush portion against a particular side or surface of the interproximal space.

It is accordingly an object of the present invention to provide a tooth cleaner of a variable diameter type which is constructed to be more efficiently utilized by a user.

Another object of the present invention is to provide an interproximal space cleaner of the variable diameter type that is constructed to enable the user to minimize undesirable effects that could be caused to the cleaner, by snags or projections in an interproximental space.

A further object of the present invention is to provide a tooth cleaner of the above type which is capable of being used with a fixed bridge and/or with spaces having contact points through which the flexible string portion cannot readily pass.

Still another object of the present invention is to achieve the above objects with a tooth cleaner that may be readily and economically manufactured, is simple and convenient to use and which is easily adapted to being either inserted into a space through the contact points or by being pushed into and through a space.

In carrying out the present invention, the tooth cleaner includes as disclosed in the heretofore mentioned patent application, a unitary length of a plurality of individual filaments. A portion of the cleaner has the filaments crinkled and randomly distorted providing a variable diameter brush portion while the remainder of the cleaner has the filaments straight and parallel and capable of somewhat ready separation to enable the string portion to pass through the contact points of adjacent teeth. A hardened covering is formed on the filaments and the covering maintains the string portion filaments straight and parallel while adding abrasiveness and resilience to the variable diameter brush portion.

In the heretofore suggested constructions of such a cleaner, the brush portion had been positioned at one end while the string portion extended therefrom and in use the user normally uses only the string portion to pull the brush through the space in one direction. If, in use, the brush portion had some filaments that caught on rough projections on the teeth surfaces, the user, basically was forced or by habit, would continue the pulling of the cleaner in the same direction which sometimes broke the snagged filaments. Continued pulling freed them from the other filaments of the cleaner and they remained snagged in the spaces.

In accordance with the present invention, however, the brush portion is located intermediate the cleaner with the string portion being in two parts to have a string part connected to both ends thereof. Thus, the user may, by the use of either string portion pull the cleaner through a space in either direction and if a snag develops, simply reverse the direction of movement by pulling on the other string part. Moreover, if a user should inadvertently pull so as to cause breakage of some filaments, the broken snagged filaments will tend to remain still secured to the string parts and thus would tend to be pulled away from the snag with the cleaner thereby eliminating or minimizing the possibility that a broken filament will remain within the space. Moreover, a broken filament, even if separated from the cleaner, is more readily removed from the dental space, as it has a longer length and hence more accessibility for grasping by the user.

In a further embodiment of the invention, at least one end extent and, perhaps, both of the string parts is made rigid rather than being left flexible in order to permit a user to push the end through a space where the string portion could not enter. Such a possibility occurs when a fixed bridge joins the top or other surfaces of the teeth or where the contact points are too tight to permit insertion. In this manner, the rigid end portion may be inserted into and through the space to be grasped by the user for pulling the remainder of the cleaner through the space.

Other features and advantages will hereinafter appear.

In the drawing

Figure 1:
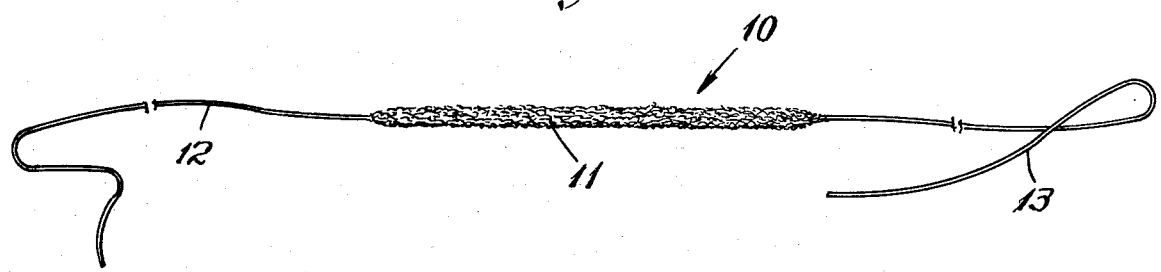
FIG. 1 is an elevation of a tooth cleaner of the present invention.

Referring to the drawing, an embodiment of the cleaner of the present invention shown in FIG. 1 is generally indicated by the reference numeral 10 and includes a brush portion 11 and a string portion that includes two parts 12 and 13. The string parts are positioned on either side of the brush portion and the cleaner is constructed as disclosed in my prior noted application. Thus, instead of, as disclosed therein, severing a continuous length of alternating string and brush portions at the brush portions, the length is separated into cleaners by cutting intermediate the string portions.

With the above construction it will be appreciated that if, for example, the user forces the part 13 within a dental space and is pulling thereon, if any filaments of the brush portion 11 should snag on a projection in the space, the user may simply reverse the movement of the cleaner by pulling on the string part 12. Moreover, if too much force has been exerted after some filaments of the brush portion have encountered a snag and breaks, then the user by pulling on the string part 12 with which the snagged or broken filaments are still unitary, generally can pull the broken filaments away from the snag thus preventing the broken filaments from being stuck within the space. Moreover, even if a user should continue pulling on the part 13, and separated the broken filaments from the rest of the cleaner, such separated filaments will have such a large extent as to provide accessibility for a user to readily grasp and remove it from the space.

Figure 2:
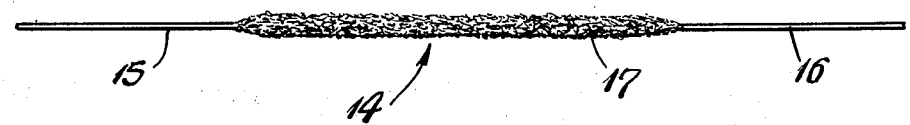
FIG. 2 is a view of another embodiment of the tooth cleaner which enables an end of the cleaner to be forced in and through a dental space.

Shown in FIG. 2 is a further embodiment of the present invention of a tooth cleaner in which the cleaner 14 is formed of two string parts 15 and 16 with a brush portion 17 located therebetween. The hardened covering disclosed in the above-noted application is applied to the length of the cleaner and, in addition, a second or even a third coating of the hardenable covering is applied at least on the string portions 15 and 16. The thickness of the covering is such that it causes the string parts 15 and 16 to be essentially rigid. Thus a user can grasp a string part and push it into and through a space where it can be grasped on the other side and pulled to draw the cleaner through the space. This embodiment of the invention is utilized where a user is unable to reasonably force the flexible portion of the cleaner shown in FIG. 1 through the contact points of a space or the space is bridged by a dental struction. If desired, as shown in FIG. 2, the extent of the string parts may be quite short, on the order of 2 inches or so.

Figure 3:
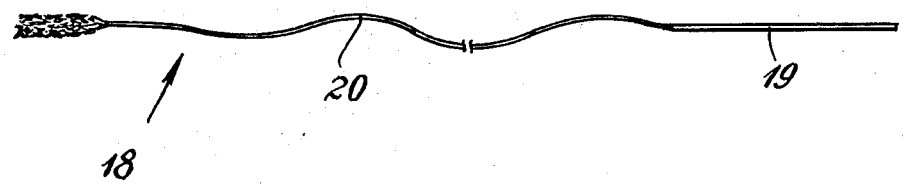
FIG. 3 is a further embodiment of a string part of the cleaner.

Shown in FIG. 3 is an embodiment of a string part 18 in which its free end extent 19 is made rigid by the use of a sufficient thickness of covering material as were the parts 15 and 16. The remainder of the part 18 indicated by the reference numeral 20 is flexible as were the parts 12 and 13. Such a string part enables the cleaner to be either passed through the contact points by way of the flexible remainder 20 or to be forced into and through a crevice by way of the rigid end extent 19.

Thus a cleaner, if desired, may have both all flexible string parts, both all rigid string parts, or both a portion flexible end, a portion rigid, or a combination thereof.

By having two string parts, it should be noted that a user by grasping both can move the brush portion back and forth in the space and/or force the cleaner against one of the surfaces defining the space to perhaps increase the efficiency of the cleaner.

As disclosed in my above noted application, the filaments may be formed of plastic material such as "Nylon" and the hardenable covering consist of "Nylon" resin dissolved in an evaporable alcohol.

It will accordingly be understood that there has been disclosed a tooth cleaner for passage through an interproximal space. The user is able to easily pull the cleaner in either direction, minimize if not completely eliminate the possibility of some filaments being broken and left in the space and utilize the cleaner with greater efficiency. Moreover by having at least one end extent of one of the string parts rigid, the cleaner may be used in spaces in which the flexible portion could not heretofore enter.

Variations and modifications may be made within the scope of the claims and portions of the improvements may be used without others.

I claim:

1. A teeth cleaner for passage through interproximal space formed between adjacent teeth comprising an elongate flexible string portion and an elongate brush portion secured to the string portion, said brush portion being of spongy elastic material formed to have a cross-sectional extent normally substantially larger than the cross-section extent of the string portion and formed of a plurality of textured, commingled filaments that have been permanently deformed and crinkled, in which the string portion is formed of a plurality of essentially straight filaments that are unitary with the filaments of the brush part, in which the string portion has two parts, one at each end of the brush portion with both string parts each having an extent that is sufficient to enable grasping thereof by a user and in which there is a hardened covering on at least one of the string portions with the hardened covering being thicker on at least an end extent of the one of the string parts than on the remainder of the string portion with the hardened covering having sufficient thickness to cause the string part extent to be essentially rigid to enable a user to push on the extent.

* * * * *